United States Patent

Maurer et al.

[11] 4,079,129
[45] Mar. 14, 1978

[54] O-ALKYL-O-(2-CARBALKOXY-2-ALKOXY-VINYL)-(THIONO) (THIOL)PHOSPHORIC (PHOSPHONIC) ACID ESTERS AND METHOD OF COMBATING PESTS

[75] Inventors: Fritz Maurer; Hans-Jochem Riebel, both of Wuppertal; Ingeborg Hammann, Cologne; Wolfgang Behrenz, Overath-Steinenbrueck; Bernhard Homeyer, Leverkusen, all of Germany

[73] Assignee: Bayer Aktiengesellschaft, Leverkusen, Germany

[21] Appl. No.: 704,257

[22] Filed: Jul. 12, 1976

[30] Foreign Application Priority Data

Jul. 26, 1975  Germany .............................. 2533601

[51] Int. Cl.² .......................... A01N 9/36; C07F 9/40; C07F 9/165
[52] U.S. Cl. .................... 424/212; 260/940; 260/941
[58] Field of Search ......................... 260/941; 424/212

[56] References Cited

U.S. PATENT DOCUMENTS

| | | | |
|---|---|---|---|
| 2,867,646 | 1/1959 | Whetstone et al. ................. | 260/941 |
| 3,053,729 | 9/1962 | Sun ................................. | 260/941 UX |
| 3,450,801 | 6/1969 | Dawson et al. ..................... | 260/941 |
| 3,733,376 | 5/1973 | Kristiansen et al. ................. | 260/941 |
| 3,784,589 | 1/1974 | Large ................................. | 260/941 |

*Primary Examiner*—Anton H. Sutto
*Attorney, Agent, or Firm*—Burgess, Dinklage & Sprung

[57] ABSTRACT

O-Alkyl-O-(2-carbalkoxy-2-alkoxy-vinyl)-(thiono)(-thiol) phosphoric (phosphonic) acid esters of the formula

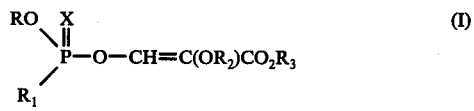

in which
  R, $R_2$ and $R_3$ each independently is alkyl with 1 to 6 carbon atoms,
  $R_1$ is alkyl with 1 to 4 carbon atoms, alkylthio with 1 to 6 carbon atoms, or phenyl, and
  X is oxygen or sulfur, which possess insecticidal, acaricidal and nematicidal properties.

9 Claims, No Drawings

O-ALKYL-O-(2-CARBALKOXY-2-ALKOXY-VINYL)-(THIONO) (THIOL)PHOSPHORIC (PHOSPHONIC) ACID ESTERS AND METHOD OF COMBATING PESTS

The present invention relates to and has for its objects the provision of particular new O-alkyl-O-(2-carbalkoxy-2-alkoxy-vinyl)-(thiono)(thiol)phosphoric(phosphonic) acid esters which possess insecticidal, acaricidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known that 2-carboalkoxy-2-cyano-vinyl-phosphoric (phosphonic) acid esters, for example O,O-diethyl-O-[1-methyl-2-cyano-2-carbethoxyvinyl]-phosphoric acid ester (Compound A) and O-ethyl-O-[1-methyl-2-carbethoxy-2-cyanovinyl]-ethane-phosphonic acid ester (Compound B) (Belgian patent specification No. 654,748) and O,O-diethyl-O-(2-ethoxy-2-carbethoxyvinyl)-thionophosphoric acid ester (Compound C) (Belgian patent specification No. 755,934), as well as O,O-dimethyl- (Compound D) and O,O-diethyl-S-(1-ethylthio-1-carbethoxymethyl)-thionothiolphosphoric acid esters (Compound E) (German Published Specification DAS No. 1,068,699) and O,O-dimethyl-S-(1,2-dicarbethoxyethyl)-thionothiolphosphoric acid ester (Compound F) (U.S. Pat. No. 2,578,652), have insecticidal and acaricidal properties.

The present invention provides, as new compounds, the vinyl(thiono)(thiol)phosphoric(phosphonic) acid esters of the general formula

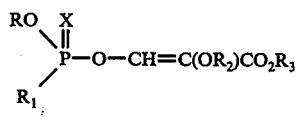

in which

R, $R_2$ and $R_3$ each independently is alkyl with 1 to 6 carbon atoms, $R_1$ is alkyl with 1 to 4 carbon atoms, alkylthio with 1 to 6 carbon atoms, or phenyl, and X is oxygen or sulfur.

The general formula (I) here includes the corresponding cis- and trans-isomers of the structures (II) and (III) and the mixtures of these components:

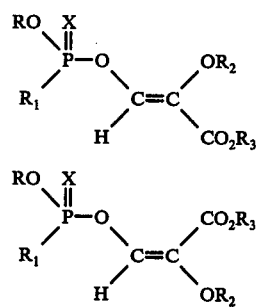

Preferably, R and $R_2$ independently of one another, each represents straight-chain or branched alkyl with 1 to 5 carbon atoms, $R_3$ represents straight-chain or branched alkyl with 1 to 4 carbon atoms, $R_1$ represents straight-chain or branched alkyl or alkylthio, each with 1 to 4 carbon atoms, or phenyl and X represents sulfur.

Surprisingly, the vinyl(thiono)(thiol)phosphoric(phosphonic) acid esters according to the invention exhibit a better insecticidal, acaricidal and nematicidal action than corresponding previously known compounds of analogous structure and of the same type of action. The products according to the present invention thus represent a genuine enrichment of the art.

The present invention also provides a process for the preparation of a vinyl(thiono)(thiol)phosphoric(phosphonic) acid ester of the formula (I) in which a (thiono)(thiol) phosphoric(phosphonic) acid ester halide of the general formula

in which

R, $R_1$ and X have the above-mentioned meanings and

Hal represents halogen, preferably chlorine, is reacted with a 1-alkoxy-1-formylacetic acid alkyl ester derivative of the formula (V) or its enol form (VI)

or

in which $R_2$ and $R_3$ have the above-mentioned meanings and

M represents hydrogen or one equivalent of an alkali metal, alkaline earth metal or ammonium, if appropriate in the presence of an acid acceptor and if appropriate in the presence of a solvent or diluent.

If, for example, O-ethyl-S-n-propyl-phosphoric acid diester chloride and 1-formyl-1-ethoxy-acetic acid ethyl ester are used as starting materials, the course of the reaction can be represented by the following equation:

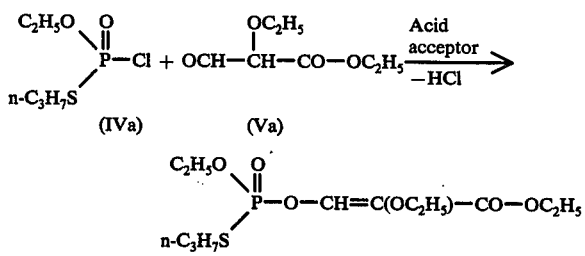

The (thiono)(thiol)phosphoric(phosphonic) acid ester halides (IV) required as starting materials are known and can be prepared in accordance with customary processes.

The following may be mentioned as individual examples: O,S-dimethyl-, O,S-diethyl-, O,S-di-n-propyl-, O,S-di-isopropyl-, O,S-di-n-butyl-, O,S-di-isobutyl-, O,S-di-tert.-butyl-, O,S-di-n-pentyl-, O-ethyl-S-n-propyl-, O-ethyl-S-isopropyl-, O-ethyl-S-n-butyl-, O-ethyl-S-sec.-butyl-, O-n-propyl-S-ethyl-, O-n-propyl-S-isopropyl-, O-n-butyl-S-n-propyl- and O-sec.-butyl-S-ethyl-thiolphosphoric acid diester chloride and the corresponding thiono analogues, and also O-methyl-, O-ethyl-, O-n-propyl-, O-isopropyl-, O-n-butyl-, O-isobutyl-, O-sec.-butyl-, O-tert.-butyl- and O-n-pentyl-methane-, ethane-, n-propane-, isopropane-, n-butane-, isobutane-, tert.-butane-, sec.-butane- and benzene-phosphonic acid ester chloride and the corresponding thiono analogues.

The 1-alkoxy-1-formylacetic acid alkyl ester derivatives (V) can be prepared by condensation of 1-alkoxyacetic acid alkyl esters with the corresponding formic acid alkyl esters, if appropriate in the presence of alcoholates.

The following may be mentioned as individual examples: 1-methoxy-, 1-ethoxy-, 1-n-propoxy-, 1-isopropoxy-, 1-n-butoxy-, 1isobutoxy-, 1-sec.-butoxy-, 1-tert.-butoxy- and 1-n-pentoxy-1-formylacetic acid methyl ester, ethyl ester, n-propyl ester, isopropyl ester, n-butyl ester, isobutyl ester and sec.-butyl ester.

The process for the preparation of the compounds according to the invention is preferably carried out in the presence of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 120° C, preferably at from 25° to 60° C.

In general, the reaction is allowed to take place under normal pressure.

In a preferred method of carrying out the process, the alkoxyformylacetic acid alkyl ester derivative (V), preferably in 10% excess, together with the acid acceptor, is introduced into one of the above solvents and the phosphoric acid derivative (IV) is added dropwise to the mixture. After completion of the reaction at the stated temperatures, the reaction mixture is poured into an organic solvent, for example toluene, and the solution is worked up in accordance with customary methods by washing and drying the organic phase and distilling off the solvent.

The new compounds are obtained in the form of oils, which in part cannot be distilled without decomposition but are freed from the last volatile constituents by so-called "slight distillation", that is to say by prolonged heating under reduced pressure to moderately elevated temperatures, and are purified in this way. They are characterized by the refractive index.

As already mentioned, the vinyl(thiono)(thiol)phosphoric (phosphonic) acid esters according to the invention are distinguished by an excellent insecticidal, acaricidal and nematicidal activity. They are active against plant pests, pests harmful to health and pests of stored products and combine a low phytotoxicity with a good action against both sucking and biting insects and mites.

For this reason, the compounds according to the invention can be employed successfully as pesticides in plant protection and in the hygiene field and the field of protection of stored products.

To the sucking insects there belong, in the main aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cottong bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (*Lepidoptera*) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cut-worm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuehniella*) and greater wax moth (*Galleria mellonella*).

Also to be classed with the biting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (Oryzaephilus surinamensis), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (*Tetranychidae*) such as the two-spotted spider mite (*Tetranychus urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the process products are also distinguished by an outstanding residual activity on wood and clay, as well as a good stability to alkali on limed substrates.

The active compounds according to the invention couple a low toxicity to warm-blooded animals with powerful nematicidal properties and can therefore be used to combat nematodes, especially phytopathogenic nematodes. These essentially include leaf nematodes (Arphelenchoides), such as the chrysanthemum eelworm (*A. ritzemabosi*), the leaf-blotch eelworm (*A. fragariae*) and the rice eelworm (*A. oryzae*); stem nematodes (Ditylenchus), such as the stem eelworm (*D. Dipsaci*); root-knot nematodes (Meloidogyne), such as *M. arenaria* and *M. incognita*; cyst-forming nematodes (Heterodera), such as the potato cyst eelworm (*H. rostochiensis*) and the beet cyst eelworm (*H. schachtii*); and also free-living root nematodes, for example of the genera Pratylenchus, Paratylenchus, Rotylenchus, Xiphinema and Radopholus.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority, and outstanding activity of the particular new compounds of the present invention are illustrated, without limitation, by the following examples:

EXAMPLE 1

Drosophila test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed; 0% means that no flies were killed.

The active compounds, the concentrations of the active compounds, the evaluation times and the results can be seen from the following table:

Table 1

| Active compound | | Active compound concentration in % | Degree of destruction in % after 1 day |
|---|---|---|---|
| $(C_2H_5O)_2\overset{\overset{O}{\|\|}}{P}-O-C(CH_3)=C(CN)-CO-OC_2H_5$ (known) | (A) | 0.01<br>0.001 | 100<br>0 |
| $\overset{C_2H_5O}{\underset{C_2H_5}{>}}\overset{\overset{O}{\|\|}}{P}-O-C(CH_3)=C(CN)-CO-OC_2H_5$ (known) | (B) | 0.01<br>0.001 | 100<br>0 |
| $\overset{CH_3}{\underset{C_2H_5O}{>}}\overset{\overset{S}{\|\|}}{P}-O-CH=C\overset{OC_2H_5}{\underset{CO-OC_2H_5}{<}}$ | (3) | 0.01<br>0.001 | 100<br>100 |
| $\overset{CH_3}{\underset{n-C_3H_7O}{>}}\overset{\overset{S}{\|\|}}{P}-O-CH=C\overset{OC_2H_5}{\underset{CO-OC_2H_5}{<}}$ | (34) | 0.01<br>0.001 | 100<br>100 |
| $\overset{CH_3O}{\underset{C_2H_5}{>}}\overset{\overset{S}{\|\|}}{P}-O-CH=C\overset{OC_2H_5}{\underset{CO-OC_2H_5}{<}}$ | (4) | 0.01<br>0.001 | 100<br>100 |
| $\overset{C_2H_5O}{\underset{C_2H_5}{>}}\overset{\overset{S}{\|\|}}{P}-O-CH=C\overset{OC_2H_5}{\underset{CO-OC_2H_5}{<}}$ | (1) | 0.01<br>0.001 | 100<br>100 |
| $\overset{C_2H_5}{\underset{n-C_3H_7O}{>}}\overset{\overset{S}{\|\|}}{P}-O-CH=C\overset{OC_2H_5}{\underset{CO-OC_2H_5}{<}}$ | (5) | 0.01<br>0.001 | 100<br>100 |
| $\overset{C_2H_5}{\underset{iso-C_4H_9O}{>}}\overset{\overset{S}{\|\|}}{P}-O-CH=C\overset{OC_2H_5}{\underset{CO-OC_2H_5}{<}}$ | (30) | 0.01<br>0.001 | 100<br>100 |

Table 1-continued
(*Drosophila* test)

| Active compound | | Active compound concentration in % | Degree of destruction in % after 1 day |
|---|---|---|---|
| $(CH_3)(C_2H_5O)P(S)-O-CH=C(OCH_3)-CO-OC_2H_5$ | (27) | 0.01<br>0.001 | 100<br>100 |
| $(CH_3)(iso\text{-}C_3H_7O)P(S)-O-CH=C(OCH_3)-CO-OC_2H_5$ | (28) | 0.01<br>0.001 | 100<br>100 |
| $(C_2H_5)(C_2H_5O)P(S)-O-CH=C(OCH_3)-CO-OC_2H_5$ | (26) | 0.01<br>0.001 | 100<br>100 |
| $(C_2H_5O)(n\text{-}C_3H_7S)P(S)-O-CH=C(OCH_3)-CO-OC_2H_5$ | (29) | 0.01<br>0.001 | 100<br>100 |
| $(CH_3)(C_2H_5O)P(S)-O-CH=C(OC_2H_5)-CO-OCH_3$ | (25) | 0.01<br>0.001 | 100<br>100 |
| $(CH_3)(iso\text{-}C_3H_7O)P(S)-O-CH=C(OC_2H_5)-CO-OCH_3$ | (23) | 0.01<br>0.001 | 100<br>100 |
| $(CH_3O)(C_2H_5)P(S)-O-CH=C(OC_2H_5)-CO-OCH_3$ | (24) | 0.01<br>0.001 | 100<br>100 |
| $(C_2H_5O)(C_2H_5)P(S)-O-CH=C(OC_2H_5)-CO-OCH_3$ | (22) | 0.01<br>0.001 | 100<br>100 |
| $(CH_3)(C_2H_5O)P(S)-O-CH=C(OC_2H_5)-CO-OC_3H_7\text{-}iso$ | (10) | 0.01<br>0.001 | 100<br>100 |
| $(CH_3O)(C_2H_5)P(S)-O-CH=C(OC_2H_5)-CO-OC_3H_7\text{-}iso$ | (12) | 0.01<br>0.001 | 100<br>100 |
| $(C_2H_5O)(C_2H_5)P(S)-O-CH=C(OC_2H_5)-CO-OC_3H_7\text{-}iso$ | (8) | 0.01<br>0.001 | 100<br>100 |
| $(C_2H_5)(n\text{-}C_3H_7O)P(S)-O-CH=C(OC_2H_5)-CO-OC_3H_7\text{-}iso$ | (11) | 0.01<br>0.001 | 100<br>100 |
| $(CH_3)(C_2H_5O)P(S)-O-CH=C(OC_4H_9\text{-}n)-CO-OC_2H_5$ | (15) | 0.01<br>0.001 | 100<br>100 |
| $(C_2H_5)(CH_3O)P(S)-O-CH=C(OC_4H_9\text{-}n)-CO-OC_2H_5$ | (14) | 0.01<br>0.001 | 100<br>99 |
| $(C_2H_5)(C_2H_5O)P(S)-O-CH=C(OC_4H_9\text{-}n)-CO-OC_2H_5$ | (13) | 0.01<br>0.001 | 100<br>100 |
| $(CH_3)(C_2H_5O)P(S)-O-CH=C(OC_4H_9\text{-}sec.)-CO-OC_2H_5$ | (20) | 0.01<br>0.001 | 100<br>100 |
| $(CH_3O)(C_2H_5)P(S)-O-CH=C(OC_4H_9\text{-}sec.)-CO-OC_2H_5$ | (19) | 0.01<br>0.001 | 100<br>100 |

Table 1-continued

| Active compound | | (Drosophila test) Active compound concentration in % | Degree of destruction in % after 1 day |
|---|---|---|---|
| $C_2H_5\underset{C_2H_5O}{\overset{S}{\diagdown}}\hspace{-2pt}\overset{\|}{P}\hspace{-2pt}-O-CH=C\underset{CO-OC_2H_5}{\overset{OC_4H_9\text{-sec.}}{\diagup}}$ | (18) | 0.01<br>0.001 | 100<br>100 |

EXAMPLE 2

Phaedon larvae test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dripping wet and were then infested with mustard beetle larvae (Phaedon cochleariae).

After the specified periods of time, the degree of destruction was determined in %: 100% means that all of the beetle larvae had been killed whereas 0% means that none of the beetle larvae had been killed.

The active compounds, the concentrations of the active compounds, the evaluation times and the results can be seen from the following table:

Table 2

| Active compound | | (Phaedon larvae test) Active compound concentration in % | Degree of destruction in % after 3 days |
|---|---|---|---|
| $(C_2H_5O)_2\overset{O}{\overset{\|}{P}}-O-\underset{CH_3}{\overset{\|}{C}}=C-(CN)-CO-OC_2H_5$<br>(known) | (A) | 0.1<br>0.01 | 100<br>0 |
| $\underset{C_2H_5O}{\overset{CH_3}{\diagdown}}\hspace{-2pt}\overset{S}{\overset{\|}{P}}\hspace{-2pt}-O-CH=C\underset{CO-OC_2H_5}{\overset{OC_2H_5}{\diagup}}$ | (3) | 0.1<br>0.01 | 100<br>100 |
| $\underset{n-C_3H_7O}{\overset{CH_3}{\diagdown}}\hspace{-2pt}\overset{S}{\overset{\|}{P}}\hspace{-2pt}-O-CH=C\underset{CO-OC_2H_5}{\overset{OC_2H_5}{\diagup}}$ | (34) | 0.1<br>0.01 | 100<br>100 |
| $\underset{C_2H_5}{\overset{CH_3O}{\diagdown}}\hspace{-2pt}\overset{S}{\overset{\|}{P}}\hspace{-2pt}-O-CH=C\underset{CO-OC_2H_5}{\overset{OC_2H_5}{\diagup}}$ | (4) | 0.1<br>0.01 | 100<br>100 |
| $\underset{C_2H_5}{\overset{C_2H_5O}{\diagdown}}\hspace{-2pt}\overset{S}{\overset{\|}{P}}\hspace{-2pt}-O-CH=C\underset{CO-OC_2H_5}{\overset{OC_2H_5}{\diagup}}$ | (1) | 0.1<br>0.01 | 100<br>100 |
| $\underset{n-C_3H_7O}{\overset{C_2H_5}{\diagdown}}\hspace{-2pt}\overset{S}{\overset{\|}{P}}\hspace{-2pt}-O-CH=C\underset{CO-OC_2H_5}{\overset{OC_2H_5}{\diagup}}$ | (5) | 0.1<br>0.01 | 100<br>100 |
| $\underset{C_2H_5O}{\overset{n-C_3H_7S}{\diagdown}}\hspace{-2pt}\overset{S}{\overset{\|}{P}}\hspace{-2pt}-O-CH=C\underset{CO-OC_2H_5}{\overset{OC_2H_5}{\diagup}}$ | (7) | 0.1<br>0.01 | 100<br>100 |
| $\underset{iso-C_4H_9O}{\overset{C_2H_5}{\diagdown}}\hspace{-2pt}\overset{S}{\overset{\|}{P}}\hspace{-2pt}-O-CH=C\underset{CO-OC_2H_5}{\overset{OC_2H_5}{\diagup}}$ | (30) | 0.1<br>0.01 | 100<br>100 |
| $\underset{C_2H_5O}{\overset{CH_3}{\diagdown}}\hspace{-2pt}\overset{S}{\overset{\|}{P}}\hspace{-2pt}-O-CH=\underset{CO-OC_2H_5}{\overset{OCH_3}{\overset{\|}{C}}}$ | (27) | 0.1<br>0.01 | 100<br>100 |
| $\underset{C_2H_5O}{\overset{C_2H_5}{\diagdown}}\hspace{-2pt}\overset{S}{\overset{\|}{P}}\hspace{-2pt}-O-CH=\underset{CO-OC_2H_5}{\overset{OCH_3}{\overset{\|}{C}}}$ | (26) | 0.1<br>0.01 | 100<br>100 |
| $\underset{iso-C_3H_7O}{\overset{CH_3}{\diagdown}}\hspace{-2pt}\overset{S}{\overset{\|}{P}}\hspace{-2pt}-O-CH=C\underset{CO-OCH_3}{\overset{OC_2H_5}{\diagup}}$ | (23) | 0.1<br>0.01 | 100<br>100 |

Table 2-continued
(*Phaedon* larvae test)

| Active compound | | Active compound concentration in % | Degree of destruction in % after 3 days |
|---|---|---|---|
| (C₂H₅O)(C₂H₅)P(=S)—O—CH=C(OC₂H₅)(CO—OCH₃) | (22) | 0.1<br>0.01 | 100<br>100 |
| (CH₃)(C₂H₅O)P(=S)—O—CH=C(OC₂H₅)(CO—OC₃H₇-iso) | (10) | 0.1<br>0.01 | 100<br>100 |
| (CH₃O)(C₂H₅)P(=S)—O—CH=C(OC₂H₅)(CO—OC₃H₇-iso) | (12) | 0.1<br>0.01 | 100<br>100 |
| (C₂H₅)(n-C₃H₇O)P(=S)—O—CH=C(OC₂H₅)(CO—OC₃H₇-iso) | (11) | 0.1<br>0.01 | 100<br>100 |
| (CH₃)(C₂H₅O)P(=S)—O—CH=C(OC₄H₉-n)(CO—OC₂H₅) | (15) | 0.1<br>0.01 | 100<br>100 |
| (C₂H₅)(CH₃O)P(=S)—O—CH=C(OC₄H₉-n)(CO—OC₂H₅) | (14) | 0.1<br>0.01 | 100<br>100 |
| (C₂H₅)(C₂H₅O)P(=S)—O—CH=C(OC₄H₉-n)(CO—OC₂H₅) | (13) | 0.1<br>0.01 | 100<br>100 |
| (n-C₃H₇S)(C₂H₅O)P(=S)—O—CH=C(OC₄H₉-n)(CO—OC₂H₅) | (16) | 0.1<br>0.01 | 100<br>100 |
| (CH₃)(C₂H₅O)P(=S)—O—CH=C(OC₄H₉-sec.)(CO—OC₂H₅) | (20) | 0.1<br>0.01 | 100<br>100 |
| (CH₃O)(C₂H₅)P(=S)—O—CH=C(OC₄H₉-sec.)(CO—OC₂H₅) | (19) | 0.1<br>0.01 | 100<br>100 |
| (C₂H₅)(C₂H₅O)P(=S)—O—CH=C(OC₄H₉-sec.)(CO—OC₂H₅) | (18) | 0.1<br>0.01 | 100<br>100 |
| (C₂H₅O)(n-C₃H₇S)P(=S)—O—CH=C(OC₄H₉-sec.)(CO—OC₂H₅) | (21) | 0.1<br>0.01 | 100<br>100 |

EXAMPLE 3

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 3

| Active compound | (Myzus test) | Active compound concentration in % | Degree of destruction in % after 1 day |
|---|---|---|---|
| (C$_2$H$_5$O)$_2$P(O)—O—C(CH$_3$)=C(CN)—CO—OC$_2$H$_5$ (known) | (B) | 0.1<br>0.01 | 100<br>0 |
| (CH$_3$)(C$_2$H$_5$O)P(S)—O—CH=C(OC$_2$H$_5$)(CO—OC$_2$H$_5$) | (3) | 0.1<br>0.01 | 100<br>100 |
| (C$_2$H$_5$)(n-C$_3$H$_7$O)P(S)—O—CH=C(OC$_2$H$_5$)(CO—OC$_2$H$_5$) | (5) | 0.1<br>0.01 | 100<br>100 |
| (n-C$_3$H$_7$S)(C$_2$H$_5$O)P(S)—O—CH=C(OC$_2$H$_5$)(CO—OC$_2$H$_5$) | (7) | 0.1<br>0.01 | 100<br>100 |
| (C$_2$H$_5$O)(C$_6$H$_5$)P(S)—O—CH=C(OC$_2$H$_5$)(CO—OC$_2$H$_5$) | (2) | 0.1<br>0.01 | 100<br>100 |
| (CH$_3$)(C$_2$H$_5$O)P(S)—O—CH=C(OCH$_3$)—CO—OC$_2$H$_5$ | (27) | 0.1<br>0.01 | 100<br>100 |
| (CH$_3$)(iso-C$_3$H$_7$O)P(S)—O—CH=C(OCH$_3$)—CO—OC$_2$H$_5$ | (28) | 0.1<br>0.01 | 100<br>100 |
| (C$_2$H$_5$)(C$_2$H$_5$O)P(S)—O—CH=C(OCH$_3$)—CO—OC$_2$H$_5$ | (26) | 0.1<br>0.01 | 100<br>100 |
| (C$_2$H$_5$O)(n-C$_3$H$_7$S)P(S)—O—CH=C(OCH$_3$)—CO—OC$_2$H$_5$ | (29) | 0.1<br>0.01 | 100<br>100 |
| (CH$_3$)(C$_2$H$_5$O)P(S)—O—CH=C(OC$_2$H$_5$)(CO—OCH$_3$) | (25) | 0.1<br>0.01 | 100<br>100 |
| (CH$_3$)(iso-C$_3$H$_7$O)P(S)—O—CH=C(OC$_2$H$_5$)(CO—OCH$_3$) | (23) | 0.1<br>0.01 | 100<br>100 |
| (CH$_3$O)(C$_2$H$_5$)P(S)—O—CH=C(OC$_2$H$_5$)(CO—OCH$_3$) | (24) | 0.1<br>0.01 | 100<br>100 |
| (C$_2$H$_5$O)(C$_2$H$_5$)P(S)—O—CH=C(OC$_2$H$_5$)(CO—OCH$_3$) | (22) | 0.1<br>0.01 | 100<br>100 |
| (CH$_3$O)(C$_2$H$_5$)P(S)—O—CH=C(OC$_2$H$_5$)(CO—OC$_3$H$_7$-iso) | (12) | 0.1<br>0.01 | 100<br>100 |

Table 3-continued

| Active compound | (*Myzus* test) | Active compound concentration in % | Degree of destruction in % after 1 day |
|---|---|---|---|
| $C_2H_5O$, $C_2H_5$ >P(S)-O-CH=C($OC_2H_5$)(CO-$OC_3H_7$-iso) | (8) | 0.1<br>0.01 | 100<br>100 |
| $C_2H_5$, n-$C_3H_7O$ >P(S)-O-CH=C($OC_2H_5$)(CO-$OC_3H_7$-iso) | (11) | 0.1<br>0.01 | 100<br>100 |
| $CH_3$, $C_2H_5O$ >P(S)-O-CH=C($OC_4H_9$-n)(CO-$OC_2H_5$) | (15) | 1.0<br>0.01 | 100<br>100 |
| $C_2H_5$, $CH_3O$ >P(S)-O-CH=C($OC_4H_9$-n)(CO-$OC_2H_5$) | (14) | 0.1<br>0.01 | 100<br>100 |
| $CH_3$, $C_2H_5O$ >P(S)-O-CH=C($OC_4H_9$-sec.)(CO-$OC_2H_5$) | (20) | 0.1<br>0.01 | 100<br>100 |
| $C_2H_5O$, n-$C_3H_7S$ >P(S)-O-CH=C($OC_4H_9$-sec.)(CO-$OC_2H_5$) | (21) | 0.1<br>0.01 | 100<br>100 |

EXAMPLE 4

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from the following table:

Table 4

| Active compound | (*Tetranychus* test) | Active compound concentration in % | Degree of destruction in % after 2 days |
|---|---|---|---|
| $(C_2H_5O)_2P(S)-O-CH=C(OC_2H_5)(CO-OC_2H_5)$ (known) (C) | | 0.1<br>0.01 | 98<br>0 |
| $CH_3$, $C_2H_5O$ >P(S)-O-CH=C($OC_4H_9$-n)(CO-$OC_2H_5$) | (15) | 0.1<br>0.01 | 100<br>60 |
| $CH_3$, $C_2H_5O$ >P(S)-O-CH=C($OC_4H_9$-sec.)(CO-$OC_2H_5$) | (20) | 0.1<br>0.01 | 100<br>80 |
| $CH_3$, n-$C_3H_7O$ >P(S)-O-CH=C($OC_2H_5$)(CO-$OC_2H_5$) | (34) | 0.1<br>0.01 | 100<br>55 |
| $CH_3$, iso-$C_3H_7O$ >P(S)-O-CH=C($OC_2H_5$)(CO-$OCH_3$) | (23) | 0.1<br>0.01 | 99<br>95 |

EXAMPLE 5

Critical concentration test/soil insects

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is hereinafter quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all of the test insects had been killed, and is 0% if exactly as many test insects were still alive as in the case of the untreated control.

The active compounds, amounts used and results can be seen from the table which follows:

Table 5

Critical concentration test/soil insects (*Phorbia antiqua* grubs in the soil)

| Active compound | Degree of destruction in % at an active compound concentration of 10 ppm |
|---|---|
| (D) $C_2H_5S-CH(CO-OC_2H_5)-S-P(=O)(OC_2H_5)_2$ (known) | 0 |
| (E) $C_2H_5S-CH(CO-OC_2H_5)-S-P(=S)(OCH_3)_2$ (known) | 0 |
| (F) $(CH_3O)_2P(=S)-S-CH(COOC_2H_5)-CH_2-COOC_2H_5$ (known) | 0 |
| (1) $(C_2H_5O)(C_2H_5)P(=S)-O-CH=C(OC_2H_5)(CO-OC_2H_5)$ | 100 |
| (8) $(C_2H_5O)(C_2H_5)P(=S)-O-CH=C(OC_2H_5)(CO-OC_2H_5\text{-iso})$ | 100 |
| (3) $(CH_3)(C_2H_5O)P(=S)-O-CH=C(OC_2H_5)(CO-OC_2H_5)$ | 100 |
| (4) $(CH_3O)(C_2H_5)P(=S)-O-CH=C(OC_2H_5)(CO-OC_2H_5)$ | 100 |
| (5) $(C_2H_5)(n\text{-}C_3H_7O)P(=S)-O-CH=C(OC_2H_5)(CO-OC_2H_5)$ | 100 |
| (10) $(CH_3)(C_2H_5O)P(=S)-O-CH=C(OC_2H_5)(CO-OC_2H_5\text{-iso})$ | 100 |
| (11) $(C_2H_5O)(n\text{-}C_3H_7O)P(=S)-O-CH=C(OC_2H_5)(CO-OC_2H_5\text{-iso})$ | 100 |
| (12) $(CH_3O)(C_2H_5)P(=S)-O-CH=C(OC_2H_5)(CO-OC_2H_5\text{-iso})$ | 100 |
| (13) $(C_2H_5)(C_2H_5O)P(=S)-O-CH=C(OC_4H_9\text{-n})(CO-OC_2H_5)$ | 100 |
| (14) $(C_2H_5)(CH_3O)P(=S)-O-CH=C(OC_4H_9\text{-n})(CO-OC_2H_5)$ | 100 |
| (15) $(CH_3)(C_2H_5O)P(=S)-O-CH=C(OC_4H_9\text{-n})(CO-OC_2H_5)$ | 100 |
| (18) $(C_2H_5)(C_2H_5O)P(=S)-O-CH=C(OC_4H_9\text{-sec.})(CO-OC_2H_5)$ | 100 |
| (19) $(CH_3O)(C_2H_5)P(=S)-O-CH=C(OC_4H_9\text{-sec.})(CO-OC_2H_5)$ | 100 |

Table 5-continued

Critical concentration test/soil insects
(*Phorbia antiqua* grubs in the soil)

| Active compound | | Degree of destruction in % at an active compound concentration of 10 ppm |
|---|---|---|
| 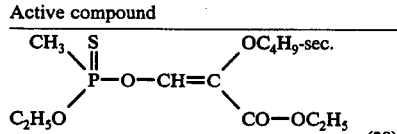 | (20) | 100 |
| 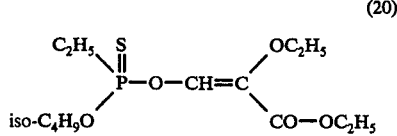 | (30) | 100 |
| 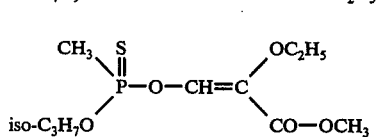 | (23) | 100 |

EXAMPLE 6

Critical concentration test/soil insects

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all of the test insects had been killed and is 0% if exactly as many test insects were still alive as in the case of the untreated control.

The active compounds, amounts used and results can be seen from the table which follows:

Table 6

Critical concentration test/soil insects
(*Tenebrio molitor* larvae in the soil)

| Active compound | | Degree of destruction in % at an active compound concentration of 20 ppm |
|---|---|---|
| 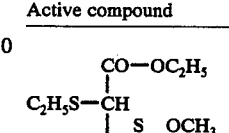 (known) | (E) | 0 |
| 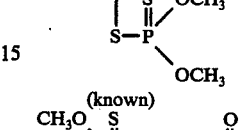 (known) | (D) | 0 |
| 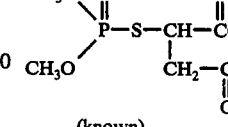 (known) | (F) | 0 |
| 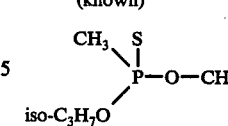 | (28) | 100 |
| 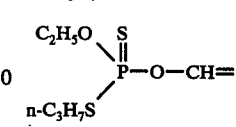 | (29) | 100 |
| 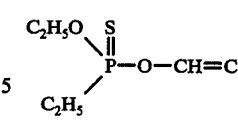 | (1) | 100 |
| 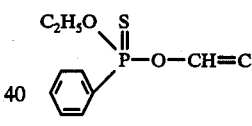 | (2) | 100 |
| 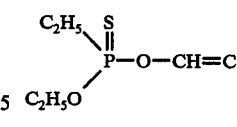 | (18) | 100 |
| 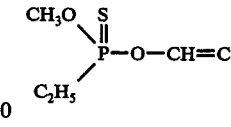 | (19) | 100 |
| 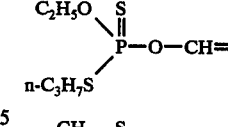 | (21) | 100 |
| 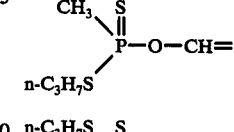 | (34) | 100 |
| 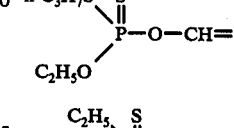 | (7) | 100 |
| 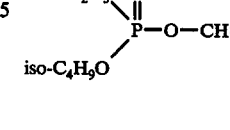 | (30) | 100 |

Table 6-continued

Critical concentration test/soil insects
(*Tenebrio molitor* larvae in the soil)

| Active compound | | Degree of destruction in % at an active compound concentration of 20 ppm |
|---|---|---|
| (iso-C$_3$H$_7$O)(CH$_3$)P(=S)—O—CH=C(OC$_2$H$_5$)(CO—OCH$_3$) | (23) | 100 |
| (C$_2$H$_5$O)(C$_2$H$_5$)P(=S)—O—CH=C(OC$_2$H$_5$)(CO—OC$_3$H$_7$-iso) | (8) | 100 |
| (C$_2$H$_5$O)(CH$_3$)P(=S)—O—CH=C(OC$_2$H$_5$)(CO—OC$_2$H$_5$) | (3) | 100 |
| (C$_2$H$_5$)(CH$_3$O)P(=S)—O—CH=C(OC$_2$H$_5$)(CO—OC$_2$H$_5$) | (4) | 100 |
| (n-C$_3$H$_7$O)(C$_2$H$_5$)P(=S)—O—CH=C(OC$_2$H$_5$)(CO—OC$_3$H$_7$-iso) | (11) | 100 |
| (C$_2$H$_5$)(CH$_3$O)P(=S)—O—CH=C(OC$_2$H$_5$)(CO—OC$_3$H$_7$-iso) | (12) | 100 |
| (C$_2$H$_5$O)(C$_2$H$_5$)P(=S)—O—CH=C(OC$_4$H$_9$-n)(CO—OC$_2$H$_5$) | (13) | 100 |
| (C$_2$H$_5$O)(CH$_3$)P(=S)—O—CH=C(OC$_4$H$_9$-n)(CO—OC$_2$H$_5$) | (15) | 100 |

EXAMPLE 7

Critical concentration test/nematodes

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm, was decisive. The soil was filled into pots, lettuce was sown in and the pots were kept at a greenhouse temperature of 27° C.

After 4 weeks, the lettuce roots were examined for infestation with nematodes (root knots), and the degree of effectiveness of the active compound was determined as a percentage. The degree of effectiveness was 100% when infestation had been completely avoided; it was 0% when the infestation was exactly the same as in the case of the control plants in untreated soil which had been infested in the same manner.

The active compounds, the amounts applied and the results can be seen from the following table:

Table 7

Critical concentration test/nematodes
(*Meloidogyne incognita*)

| Active compound | | Degree of destruction in % at an active compound concentration of 20 ppm |
|---|---|---|
| C$_2$H$_5$S—CH(CO—OC$_2$H$_5$)—S—P(=S)(OC$_2$H$_5$)(OC$_2$H$_5$) (known) | (E) | 0 |
| C$_2$H$_5$S—CH(CO—OC$_2$H$_5$)—S—P(=S)(OCH$_3$)(OCH$_3$) (known) | (D) | 0 |
| (CH$_3$O)(CH$_3$O)P(=S)—S—CH(COC$_2$H$_5$=O)—CH$_2$—COC$_2$H$_5$(=O) (known) | (F) | 0 |
| (C$_2$H$_5$O)(CH$_3$)P(=S)—O—CH=C(OC$_2$H$_5$)(CO—OC$_2$H$_5$) | (3) | 0 |
| (C$_2$H$_5$O)(C$_2$H$_5$)P(=S)—O—CH=C(OC$_4$H$_9$-sec.)(CO—OC$_2$H$_5$) | (18) | 100 |

EXAMPLE 8

LD$_{100}$ test

Test insects: *Sitophilus granarius*
Solvent: Acetone 2 parts by weight of the active compound were dissolved in 1,000 parts by volume of the solvent. The solution so obtained was diluted with further solvent to the desired concentration.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was observed 3 days after the commencement of the experiments. The destruction, in %, was determined.

The active compounds, the concentration of the active compounds, the test insects and the results can be seen from the following table:

Table 8

| Active compound | (LD$_{100}$ test/*Sitophilus granarius*) Active compound concentration of the solution in % | Degree of destruction in % |
|---|---|---|
| (B) (C$_2$H$_5$O)(C$_2$H$_5$)P(O)—O—C(CH$_3$)=C(CN)—COOC$_2$H$_5$ (known) | 0.2 | 0 |
| (4) (CH$_3$O)(C$_2$H$_5$)P(S)—O—CH=C(OC$_2$H$_5$)(COOC$_2$H$_5$) | 0.2 / 0.02 / 0.002 | 100 / 100 / 100 |
| (12) (CH$_3$O)(C$_2$H$_5$)P(S)—O—CH=C(OC$_2$H$_5$)(COOC$_3$H$_7$-iso) | 0.2 / 0.02 / 0.002 | 100 / 100 / 100 |
| (14) (C$_2$H$_5$)(CH$_3$O)P(S)—O—CH=C(OC$_4$H$_9$-n)(COOC$_2$H$_5$) | 0.2 / 0.02 | 100 / 100 |
| (19) (CH$_3$O)(C$_2$H$_5$)P(S)—O—CH=C(OC$_4$H$_9$-sec.)(COOC$_2$H$_5$) | 0.2 / 0.02 / 0.002 | 100 / 100 / 80 |
| (3) (CH$_3$)(C$_2$H$_5$O)P(S)—O—CH=C(OC$_2$H$_5$)(COOC$_2$H$_5$) | 0.2 / 0.02 / 0.002 | 100 / 100 / 100 |
| (10) (CH$_3$)(C$_2$H$_5$O)P(S)—O—CH=C(OC$_2$H$_5$)(COOC$_3$H$_7$-iso) | 0.2 / 0.02 / 0.002 | 100 / 100 / 60 |
| (15) (CH$_3$)(C$_2$H$_5$O)P(S)—O—CH=C(OC$_4$H$_9$-n)(COOC$_2$H$_5$) | 0.2 / 0.02 | 100 / 100 |
| (20) (CH$_3$)(C$_2$H$_5$O)P(S)—O—CH=C(OC$_4$H$_9$-sec.)(COOC$_2$H$_5$) | 0.2 / 0.02 | 100 / 100 |
| (22) (C$_2$H$_5$O)(C$_2$H$_5$)P(S)—O—CH=C(OC$_2$H$_5$)(COOCH$_3$) | 0.2 / 0.02 / 0.002 | 100 / 100 / 100 |
| (1) (C$_2$H$_5$O)(C$_2$H$_5$)P(S)—O—CH=C(OC$_2$H$_5$)(COOC$_2$H$_5$) | 0.2 / 0.02 / 0.002 | 100 / 100 / 100 |
| (8) (C$_2$H$_5$O)(C$_2$H$_5$)P(S)—O—CH=C(OC$_2$H$_5$)(COOC$_3$H$_7$-iso) | 0.2 / 0.02 | 100 / 100 |
| (13) (C$_2$H$_5$)(C$_2$H$_5$O)P(S)—O—CH=C(OC$_4$H$_9$-n)(COOC$_2$H$_5$) | 0.2 / 0.02 | 100 / 100 |
| (18) (C$_2$H$_5$)(C$_2$H$_5$O)P(S)—O—CH=C(OC$_4$H$_9$-sec.)(COOC$_2$H$_5$) | 0.2 / 0.02 | 100 / 100 |
| (34) (CH$_3$)(n-C$_3$H$_7$O)P(S)—O—CH=C(OC$_2$H$_5$)(COOC$_2$H$_5$) | 0.2 / 0.02 / 0.002 | 100 / 100 / 90 |

Table 8-continued

| (LD$_{100}$ test/Sitophilus granarius) | | |
|---|---|---|
| Active compound | Active compound concentration of the solution in % | Degree of destruction in % |
| $\begin{array}{c}C_2H_5\\ \diagdown\\ n\text{-}C_3H_7O\end{array}\overset{S}{\underset{\|}{P}}\text{—O—CH=C}\begin{array}{c}OC_2H_5\\ \diagdown\\ COOC_2H_5\end{array}$ (5) | 0.2<br>0.02<br>0.002 | 100<br>100<br>100 |
| $\begin{array}{c}C_2H_5\\ \diagdown\\ n\text{-}C_3H_7O\end{array}\overset{S}{\underset{\|}{P}}\text{—O—CH=C}\begin{array}{c}OC_2H_5\\ \diagdown\\ COOC_3H_7\text{-iso}\end{array}$ (11) | 0.2<br>0.02 | 100<br>100 |
| $\begin{array}{c}C_2H_5\\ \diagdown\\ \text{iso-}C_4H_9\text{—O}\end{array}\overset{S}{\underset{\|}{P}}\text{—O—CH=C}\begin{array}{c}OC_2H_5\\ \diagdown\\ COOC_2H_5\end{array}$ (30) | 0.2<br>0.02 | 100<br>100 |
| $\begin{array}{c}n\text{-}C_3H_7S\\ \diagdown\\ C_2H_5O\end{array}\overset{S}{\underset{\|}{P}}\text{—O—CH=C}\begin{array}{c}OC_2H_5\\ \diagdown\\ COOC_2H_5\end{array}$ (7) | 0.2<br>0.02 | 100<br>100 |
| $\begin{array}{c}n\text{-}C_3H_7\text{-}S\\ \diagdown\\ C_2H_5O\end{array}\overset{S}{\underset{\|}{P}}\text{—O—CH=C}\begin{array}{c}OC_4H_9\text{-}n\\ \diagdown\\ COOC_2H_5\end{array}$ (16) | 0.2<br>0.02 | 100<br>100 |
| $\begin{array}{c}C_2H_5O\\ \diagdown\\ n\text{-}C_3H_7S\end{array}\overset{S}{\underset{\|}{P}}\text{—O—CH=C}\begin{array}{c}OC_4H_9\text{-sec}\\ \diagdown\\ COOC_2H_5\end{array}$ (21) | 0.2<br>0.02 | 100<br>100 |
| $\begin{array}{c}C_2H_5O\\ \diagdown\\ C_6H_5\end{array}\overset{S}{\underset{\|}{P}}\text{—O—CH=C}\begin{array}{c}OC_2H_5\\ \diagdown\\ COOC_2H_5\end{array}$ (2) | 0.2<br>0.02 | 100<br>100 |

EXAMPLE 9

LT$_{100}$ test for Diptera

Test insects: *Musca domestica*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following table:

Table 9

| (LT$_{100}$ test for Diptera/Musca domestica) | | |
|---|---|---|
| Active compound | Active compound concentration of the solution in % | LT$_{100}$ in minutes (') or hours (hrs) |
| $\begin{array}{c}C_2H_5O\\ \diagdown\\ C_2H_5\end{array}\overset{O}{\underset{\|}{P}}\text{—O—C=C—(CN)—COOC}_2H_5$ (B)<br>$\qquad\qquad\qquad\quad\|$<br>$\qquad\qquad\qquad\ CH_3$<br>(known) | 0.2<br>0.02 | 125'<br>8 hrs |
| $\begin{array}{c}CH_3O\\ \diagdown\\ C_2H_5\end{array}\overset{S}{\underset{\|}{P}}\text{—O—CH=C}\begin{array}{c}OC_2H_5\\ \diagdown\\ COOC_2H_5\end{array}$ (4) | 0.2<br>0.02<br>0.002 | 25'<br>65'<br>160' |
| $\begin{array}{c}CH_3O\\ \diagdown\\ C_2H_5\end{array}\overset{S}{\underset{\|}{P}}\text{—O—CH=C}\begin{array}{c}OC_2H_5\\ \diagdown\\ COOC_3H_7\text{-iso}\end{array}$ (12) | 0.2<br>0.02<br>0.002 | 20'<br>55'<br>6 hrs |

Table 9-continued (LT$_{100}$ test for *Diptera/Musca domestica*)

| Active compound | | Active compound concentration of the solution in % | LT$_{100}$ in minutes (') or hours (hrs) |
|---|---|---|---|
| $\text{C}_2\text{H}_5$, CH$_3$O – P(=S) – O – CH=C(OC$_4$H$_9$-n)(COOC$_2$H$_5$) | (14) | 0.2<br>0.02 | 55'<br>150' |
| CH$_3$O, C$_2$H$_5$ – P(=S) – O – CH=C(OC$_4$H$_9$-sec.)(COOC$_2$H$_5$) | (19) | 0.2<br>0.02 | 60'<br>115' |
| CH$_3$, C$_2$H$_5$O – P(=S) – O – CH=C(OC$_2$H$_5$)(COOC$_2$H$_5$) | (3) | 0.2<br>0.02<br>0.002 | 20'<br>40'<br>6 hrs |
| CH$_3$, C$_2$H$_5$O – P(=S) – O – CH=C(OC$_2$H$_5$)(COOC$_3$H$_7$-iso) | (10) | 0.2<br>0.02<br>0.002 | 30'<br>70'<br>6 hrs |
| CH$_3$, C$_2$H$_5$O – P(=S) – O – CH=C(OC$_4$H$_9$-n)(COOC$_2$H$_5$) | (15) | 0.2<br>0.02 | 75'<br>180' |
| CH$_3$, C$_2$H$_5$O – P(=S) – O – CH=C(OC$_4$H$_9$-sec)(COOC$_2$H$_5$) | (20) | 0.2<br>0.02 | 35'<br>110' |
| C$_2$H$_5$O, C$_2$H$_5$ – P(=S) – O – CH=C(OC$_2$H$_5$)(COOCH$_3$) | (22) | 0.2<br>0.02<br>0.002 | 25'<br>60'<br>240 |
| C$_2$H$_5$O, C$_2$H$_5$ – P(=S) – O – CH=C(OC$_2$H$_5$)(COOC$_2$H$_5$) | (1) | 0.2<br>0.02<br>0.002 | 20'<br>45'<br>120' |
| C$_2$H$_5$O, C$_2$H$_5$ – P(=S) – O – CH=C(OC$_2$H$_5$)(COOC$_3$H$_7$-iso) | (8) | 0.2<br>0.02<br>0.002 | 20'<br>80'<br>6 hrs |
| C$_2$H$_5$, C$_2$H$_5$O – P(=S) – O – CH=C(OC$_4$H$_9$-n)(COOC$_2$H$_5$) | (13) | 0.2<br>0.02 | 60'<br>120' |
| C$_2$H$_5$, C$_2$H$_5$O – P(=S) – O – CH=C(OC$_4$H$_9$-sec)(COOC$_2$H$_5$) | (18) | 0.2<br>0.02 | 35'<br>95' |
| CH$_3$, n-C$_3$H$_7$O – P(=S) – O – CH=C(OC$_2$H$_5$)(COOC$_2$H$_5$) | (34) | 0.2<br>0.02 | 35'<br>100' |
| C$_2$H$_5$, n-C$_3$H$_7$O – P(=S) – O – CH=C(OC$_2$H$_5$)(COOC$_2$H$_5$) | (5) | 0.2<br>0.02<br>0.002 | 40'<br>75'<br>6 hrs |
| C$_2$H$_5$, n-C$_3$H$_7$O – P(=S) – O – CH=C(OC$_2$H$_5$)(COOC$_3$H$_7$-iso) | (11) | 0.2<br>0.02 | 35'<br>85' |

Table 9-continued

| | (LT$_{100}$ test for *Diptera/Musca domestica*) | |
|---|---|---|
| Active compound | Active compound concentration of the solution in % | LT$_{100}$ in minutes (') or hours (hrs) |
| 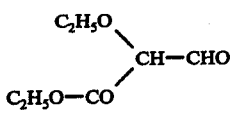 (30) | 0.2<br>0.02 | 60'<br>190' |

The process of the present invention is illustrated by the following preparative Examples.

EXAMPLE 10

(a) The 1-alkoxy-1-formylacetic acid alkyl esters (V) required as starting compounds were prepared, for example, as described below:

$$\begin{array}{c} C_2H_5O \\ \phantom{xxx}\diagdown \\ \phantom{xxxxx}CH-CHO \\ \phantom{xxx}\diagup \\ C_2H_5O-CO \end{array}$$

112 g (1 mole) of potassium tert.-butylate were added in portions to a mixture of 132 g (1 mole) of ethoxyacetic acid ethyl ester and 81.5 g (1.1 moles) of formic acid ethyl ester, in such a way that a reaction temperature did not rise above 40° C. The reaction mixture was then stirred for a further 4 hours at 20° C, subsequently poured into 1 l of water, and extracted once with 200 ml of ethylene chloride (the methylene chloride extract was discarded). The aqueous phase was acidified with hydrochloric acid while cooling with ice and was extracted with methylene chloride. After drying over sodium sulfate, the methylene chloride was stripped off. 103 g (64% of theory) of formyl-ethoxyacetic acid ethyl ester having a refractive index $n_D^{24}$ of 1.4452 were obtained.

The following compounds could be synthesized analogously:

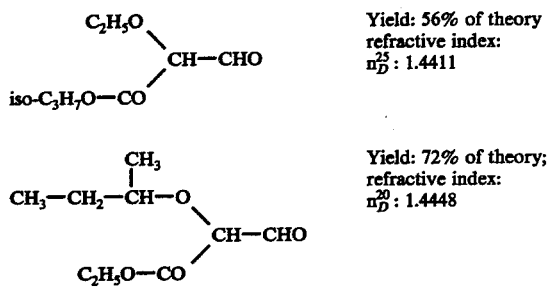

Yield: 56% of theory
refractive index:
$n_D^{25}$: 1.4411

Yield: 72% of theory;
refractive index:
$n_D^{20}$: 1.4448

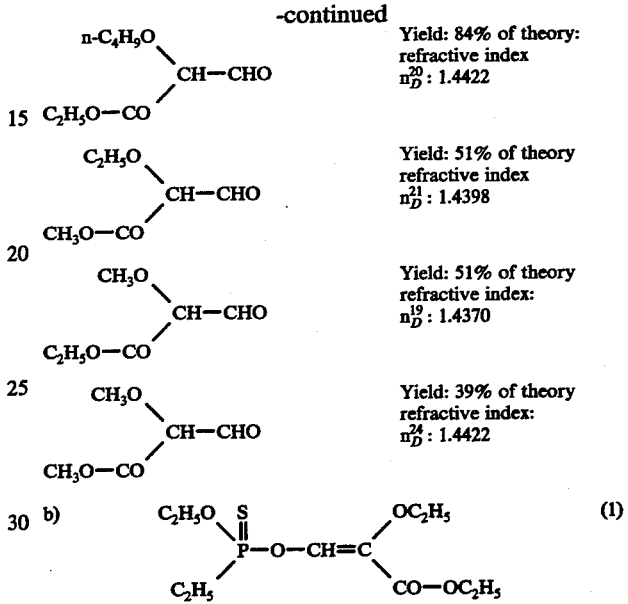

17.4 g (0.1 mole) of O-ethyl-ethanethionophosphonic acid ester chloride were added dropwise to a mixture of 17.6 g (0.11 mole) of formyl-ethoxyacetic acid ethyl ester and 16 g (0.115 mole) of potassium carbonate in 200 ml of acetonitrile. The reaction mixture was allowed to react for a further 3 hours at 40° C and was then poured into 300 ml of toluene. The toluene solution was washed with saturated sodium bicarbonate solution and water and was dried over sodium sulfate. The solvent was then stripped off and the residue was subjected to slight distillation. 22 g (74% of theory) of 0-ethyl-O-(2-carbethoxy-2-ethoxy-vinyl)-ethanethionophosphonic acid ester were obtained in the form of a yellow oil having a refractive index $n_D^{25}$ of 1.4793.

The following compounds of the general formula

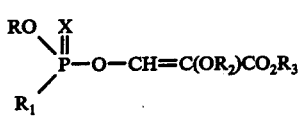 (I)

could be synthesized analogously:

| Compound No. | X | R | R$_1$ | R$_2$ | R$_3$ | Yield (% of theory) | Physical data (refractive index) |
|---|---|---|---|---|---|---|---|
| 2 | S | —C$_2$H$_5$ | —C$_6$H$_5$ | C$_2$H$_5$— | C$_2$H$_5$— | 54 | $n_D^{22}$: 1.5210 |
| 3 | S | —C$_2$H$_5$ | —CH$_3$ | C$_2$H$_5$— | C$_2$H$_5$— | 69 | $n_D^{22}$: 1,4834 |
| 4 | S | —CH$_3$ | —C$_2$H$_5$ | C$_2$H$_5$— | C$_2$H$_5$— | 70 | $n_D^{22}$: 1,4883 |
| 5 | S | —C$_3$H$_7$-n | —C$_2$H$_5$ | C$_2$H$_5$— | C$_2$H$_5$— | 74 | $n_D^{22}$: 1,4828 |
| 6 | S | —C$_3$H$_7$-iso | —CH$_3$ | C$_2$H$_5$— | C$_2$H$_5$— | 67 | $n_D^{18}$: 1,4780 |
| 7 | S | —C$_2$H$_5$ | —SC$_3$H$_7$-n | C$_2$H$_5$— | C$_2$H$_5$— | 73 | $n_D^{18}$: 1,5002 |
| 8 | S | —C$_2$H$_5$ | —C$_2$H$_5$ | C$_2$H$_5$— | isoC$_3$H$_7$— | 75 | $n_D^{25}$: 1,4763 |

-continued

| Compound No. | X | R | R₁ | R₂ | R₃ | Yield (% of theory) | Physical data (refractive index) |
|---|---|---|---|---|---|---|---|
| 9 | S | —C₂H₅ | —C₆H₅ (phenyl) | C₂H₅— | iso-C₃H₇— | 53 | $n_D^{25}$: 1,5165 |
| 10 | S | —C₂H₅ | —CH₃ | C₂H₅— | iso-C₃H₇— | 68 | $n_D^{22}$: 1,4739 |
| 11 | S | —C₃H₇-n | —C₂H₅ | C₂H₅— | iso-C₃H₇— | 55 | $n_D^{22}$: 1,4730 |
| 12 | S | —CH₃ | —C₂H₅ | C₂H₅— | iso-C₃H₇— | 37 | $n_D^{22}$: 1,4758 |
| 13 | S | —C₂H₅ | —C₂H₅ | n-C₄H₉— | C₂H₅— | 77 | $n_D^{19}$: 1,4764 |
| 14 | S | —CH₃ | —C₂H₅ | n-C₄H₉— | C₂H₅— | 65 | $n_D^{19}$: 1,4760 |
| 15 | S | —C₂H₅ | —CH₃ | n-C₄H₉— | C₂H₅— | 66 | $n_D^{19}$: 1,4759 |
| 16 | S | —C₂H₅ | —SC₃H₇-n | n-C₄H₉— | C₂H₅— | 68 | $n_D^{19}$: 1,4957 |
| 17 | S | —C₂H₅ | —C₆H₅ (phenyl) | n-C₄H₉— | C₂H₅— | 70 | $n_D^{19}$: 1,5160 |
| 18 | S | —C₂H₅ | —C₂H₅ | sec.-C₄H₉— | C₂H₅— | 74 | $n_D^{19}$: 1,4781 |
| 19 | S | —CH₃ | —C₂H₅ | sec.-C₄H₉— | C₂H₅— | 58 | $n_D^{19}$: 1,4770 |
| 20 | S | —C₂H₅ | —CH₃ | sec.-C₄H₉— | C₂H₅— | 68 | $n_D^{19}$: 1,4744 |
| 21 | S | —C₂H₅ | —SC₃H₇-n | sec.-C₄H₉— | C₂H₅— | 57 | $n_D^{19}$: 1.4977 |
| 22 | S | —C₂H₅ | —C₂H₅ | C₂H₅— | CH₃— | 75 | $n_D^{21}$: 1,4860 |
| 23 | S | —C₃H₇-iso | —CH₃ | C₂H₅— | CH₃— | 42 | $n_D^{21}$: 1,4831 |
| 24 | S | —CH₃ | —C₂H₅ | C₂H₅— | CH₃— | 48 | $n_D^{21}$: 1,4900 |
| 25 | S | —C₂H₅ | —CH₃ | C₂H₅— | CH₃— | 50 | $n_D^{21}$: 1,4881 |
| 26 | S | —C₂H₅ | —C₂H₅ | CH₃— | C₂H₅— | 73 | $n_D^{21}$: 1,4875 |
| 27 | S | —C₂H₅ | —CH₃ | CH₃— | C₂H₅— | 67 | $n_D^{21}$: 1,4864 |
| 28 | S | —C₃H₇-iso | —CH₃ | CH₃— | C₂H₅— | 67 | $n_D^{21}$: 1,4826 |
| 29 | S | —C₂H₅ | —SC₃H₇-n | CH₃— | C₂H₅— | 61 | $n_D^{20}$: 1,5076 |
| 30 | S | —C₄H₉-iso | —C₂H₅ | CH₃— | C₂H₅— | 77 | $n_D^{18}$: 1,4769 |
| 31 | S | —C₂H₅ | —C₂H₅ | CH₃— | CH₃— | 15 | $n_D^{22}$: 1,4909 |
| 32 | S | —C₂H₅ | —SC₃H₇-n | CH₃— | CH₃— | 67 | $n_D^{25}$: 1,5177 |
| 33 | S | —CH₃ | —C₂H₅ | CH₃— | C₂H₅— | 82 | $n_D^{25}$: 1,4884 |

Other compounds which can be similarly prepared include:

| Compound No. | X | R | R₁ | R₂ | R₃ |
|---|---|---|---|---|---|
| 34 | O | —CH₃ | —SC₅H₁₁-n | C₂H₅— | C₂H₅— |
| 35 | O | —C₆H₁₃-n | —SCH₃ | C₂H₅— | C₂H₅— |
| 36 | O | —C₂H₅ | —C₄H₉-sec. | C₂H₅— | C₂H₅— |
| 37 | S | —C₂H₅ | —C₂H₅ | n-C₅H₁₁— | C₂H₅— |
| 38 | S | —C₂H₅ | —C₂H₅ | n-C₃H₇— | C₂H₅— |
| 39 | S | —C₂H₅ | —C₂H₅ | n-C₆H₁₃— | C₂H₅— |
| 40 | S | —C₂H₅ | —C₂H₅ | C₂H₅— | n-C₅H₁₁— |
| 41 | S | —C₂H₅ | —C₂H₅ | C₂H₅— | sec.-C₄H₉— |
| 42 | S | —C₂H₅ | —C₂H₅ | C₂H₅— | n-C₆H₁₃— |

It will be appreciated that the instant specification and examples are set forth by way of illustration and not limitation, and that various modifications and changes may be made without departing from the spirit and scope of the present invention.

What we claim is:

1. An O-alkyl-O-(2-carbalkoxy-2-alkoxy-vinyl)-(thiono)(thiol)phosphoric(phosphonic) acid ester of the formula $$\begin{array}{c} RO \\ \diagdown \\ R_1 \end{array} \overset{X}{\underset{\parallel}{P}} {-}O{-}CH{=}C(OR_2)CO_2R_3$$

in which

R, R₂ and R₃ each independently is alkyl with 1 to 6 carbon atoms,

R₁ is alkyl with 1 to 4 carbon atoms, alkylthio with 1 to 6 carbon atoms, or phenyl, and X is oxygen or sulfur.

2. A compound according to claim 1, in which

R and R₂ each independently is alkyl with 1 to 5 carbon atoms,

R₃ is alkyl with 1 to 4 carbon atoms,

R₁ is alkyl or alkylthio each with 1 to 4 carbon atoms, or phenyl, and

X is sulfur.

3. The compound according to claim 1 wherein such compound is O-methyl-O-(2-carbethoxy-2-n-butoxyvinyl)-ethanethionophosphonic acid ester of the formula

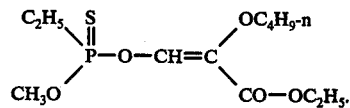

4. The compound according to claim 1 wherein such compound is O-ethyl-O-(2-carbethoxy-2-n-butoxyvinyl)-methanethionophosphonic acid ester of the formula

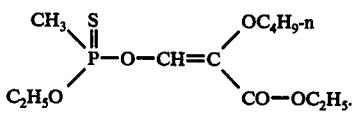

5. The compound according to claim 1 wherein such compound is O-methyl-O-(2-carbethoxy-2-sec.-butoxyvinyl)-ethanethionophosphonic acid ester of the formula

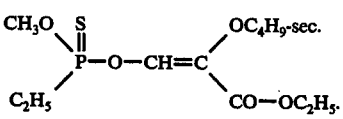

6. The compound according to claim 1 wherein such compound is O-ethyl-O-(2-carbethoxy-2-sec.-butoxyvinyl)-thiono methanephosphonic acid ester of the formula

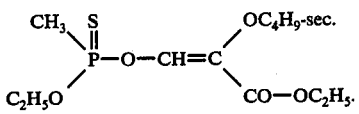

7. An insecticidal, acaricidal or nematicidal composition containing as active ingredient an insecticidally, acaricidally or nematicidally effective amount of a compound according to claim 1 in admixture with a diluent.

8. A method of combating insects, acarids or nematodes which comprises applying to the insects, acarids or nematodes, or to a habitat thereof an insecticidally, acaricidally or nematicidally effective amount of a compound according to claim 1.

9. The method according to claim 8 in which said compound is
O-ethyl-O-(2-carbethoxy-2-n-butoxy-vinyl)-methanethionophosphonic acid ester,
O-methyl-O-(2-carbethoxy-2-n-butoxy-vinyl)-ethanethionophosphonic acid ester,
O-ethyl-O-(2-carbethoxy-2-sec.-butoxy-vinyl)-methanethionophosphonic acid ester, or
O-methyl-O-(2-carbethoxy-2-sec.-butoxy-vinyl)-ethanethionophosphonic acid ester.

* * * * *